United States Patent [19]

Shimomura et al.

[11] Patent Number: 4,968,400
[45] Date of Patent: Nov. 6, 1990

[54] ENZYME SENSOR

[75] Inventors: Takeshi Shimomura; Shuichiro Yamaguchi; Naoto Uchida, all of Fuji, Japan

[73] Assignee: Terumo Kabushiki Kaisha, Tokyo, Japan

[21] Appl. No.: 359,763

[22] PCT Filed: Nov. 19, 1987

[86] PCT No.: PCT/JP87/00901
§ 371 Date: Jul. 19, 1989
§ 102(e) Date: Jul. 19, 1989

[87] PCT Pub. No.: WO88/04050
PCT Pub. Date: Jun. 2, 1988

[30] Foreign Application Priority Data

Nov. 20, 1986 [JP] Japan ............................. 61-275251

[51] Int. Cl.$^5$ ....................... G01N 27/26; C12M 1/34; C12Q 1/00
[52] U.S. Cl. .................................. 204/403; 357/25; 435/291; 435/517
[58] Field of Search ................. 435/817, 291; 357/25; 204/403, 1 E

[56] References Cited

U.S. PATENT DOCUMENTS

| | | | |
|---|---|---|---|
| 3,598,713 | 8/1971 | Baum et al. | 204/418 |
| 3,926,764 | 12/1975 | Ruzicka et al. | 204/418 |
| 3,932,233 | 1/1976 | Ruzicka et al. | 204/418 |
| 3,957,612 | 5/1976 | Niedrach et al. | 204/414 |
| 3,957,613 | 5/1976 | Macur | 204/412 |
| 4,052,285 | 10/1977 | Dobson | 204/420 |
| 4,115,209 | 9/1978 | Fraiser et al. | 204/153.1 |
| 4,198,851 | 4/1980 | Janata | 73/23 |
| 4,214,968 | 7/1980 | Battaglia et al. | 204/418 |
| 4,280,889 | 7/1981 | Szonntagh | 204/420 |
| 4,282,079 | 8/1981 | Chang et al. | 204/420 |
| 4,305,802 | 12/1981 | Koshiishi | 204/418 |
| 4,454,007 | 6/1984 | Pace | 204/153.1 |
| 4,512,870 | 4/1985 | Kohara et al. | 204/416 |
| 4,549,951 | 10/1985 | Knudson et al. | 204/416 |
| 4,561,962 | 12/1985 | Kankare | 204/415 |
| 4,563,263 | 1/1986 | Oyama et al. | 204/418 |
| 4,615,954 | 10/1986 | Solomon et al. | 429/27 |
| 4,632,732 | 12/1986 | Fog et al. | 204/153.12 |
| 4,704,193 | 11/1987 | Bowers et al. | 204/1 T |
| 4,711,245 | 12/1987 | Higgins et al. | 128/635 |
| 4,797,181 | 1/1989 | Durfor et al. | 204/1 T |
| 4,816,118 | 3/1989 | Oyama et al. | 204/418 |

FOREIGN PATENT DOCUMENTS

| | | |
|---|---|---|
| 0136362 | 4/1985 | European Pat. Off. . |
| 0186210 | 7/1986 | European Pat. Off. . |
| 3134760A | 9/1982 | Fed. Rep. of Germany . |
| 52-30490 | 3/1977 | Japan . |
| 51595 | 4/1979 | Japan . |
| 140594 | 10/1979 | Japan . |
| 57-63444 | 4/1982 | Japan . |
| 57-118153 | 7/1982 | Japan . |
| 5167951 | 10/1983 | Japan . |
| 59-164952 | 9/1984 | Japan . |
| 59-166852 | 9/1984 | Japan . |
| 59-176662 | 10/1984 | Japan . |
| 59-210356 | 11/1984 | Japan . |
| 60-52759 | 3/1985 | Japan . |
| 60-73351 | 4/1985 | Japan . |
| 898314 | 1/1982 | U.S.S.R. . |

OTHER PUBLICATIONS

Snell et al., "Surface Modified Electrodes", Chem. Soc. Rev. 1979, 8, 259–282.

(List continued on next page.)

Primary Examiner—G. L. Kaplan
Attorney, Agent, or Firm—Burns, Doane, Swecker & Mathis

[57] ABSTRACT

An insulative substrate (1) is coated with an electrically conductive layer (2) and a redox layer (3) which comprises an electrolytic polymerization film of 2,6-dimethylphenol, and the surface of the redox layer is provided with an enzyme-fixed (7). The enzyme electrode thus obtained exhibits a potentiometric response, and the enzyme-fixed layer has a strong adhesion. As a result, sensitivity is high, there is little drift and service life is prolonged. An ion-selective field-effect transistor can be used instead of the insulative substrate (1).

12 Claims, 7 Drawing Sheets

OTHER PUBLICATIONS

Faulkner, "Chemical Microstructures on Electrodes", Chem. Eng. News, 1984, 27, pp. 28–45.

Oyama et al., "Ion Selective Electrode Prepared by Motifying an Electrode with Polymers", Tokyo Seminar on Macromolecular Complexes, Tokyo, Univ. Oct. 14–1987.

*Patent Abstracts of Japan,* vol. 7, No. 48 (P-178), Feb. 24, 1983, Japanese Kokai No. 57-196,116.

Patent Abstracts of Japan, vol. 9, No. 122, May 28, 1985; Japanese Kokai, No. 60-7357.

Patent Abstracts of Japan, vol. 8, No. 159, Jul. 24, 1984; Japanese Kokai, No. 59-57156 (Apr. 2, 1984).

Oyama et al., "Electrochemical Properties of Electropolymerized Poly(1-Pyrinamine Films)" Bull Chem. Soc. Japan 59-2071-2080 (1986).

Ryan, "Electrochemical Detectors Fundamental Aspects and Analytical Application", Plenum Press, Apr. 26, 1985), p. 7.

Ma et al., "Organic Analysis Using Ion-Sensitive Electrodes", Academic Press, 1982, pp. 62 & 70, vol. 2.

Ammann, "Ion Selective Microelectrodes", Springer-Verlag, New York, pp. 5–7.

Tamura et al., "Coated Wire Sodium-and Potassium-Electrodes Based on Bis(Crown Ether) Compounds", Analytical Chemistry, vol. 54, No. 7, Jun. 1982, pp. 1224-27.

Wuthier et al., "Tin Organic Compounds as Neutral Carriers for Anion Selectrive Electrodes", Analytical Chemistry, vol. 56, No. 3, Mar. 1984, pp. 535-538.

Oyama et al., "Hydrogen Ion Selective Microelectrode Prepared by Modifying an Electrode with Polymers," Analytical Chemistry 1987, vol. 59, pp. 258-262, Jan. 1987.

Oyama, "Ion Selective Microelectrode Prepared by Modifying an Electrode with Polymers" Int. Electrical Symposium, Schaumberg, IL, May 27-29, 1987; p. 122.

Oyama et al., "A New Type of Ion-Selective Microelectrodes Using Electropolymerized Thin Films", j–4 Bioelectronalytical Chemistry Symposium, Honolulu, Oct. 18-23, 1987.

Norov et al., "Calcium-Selective Electrode Without an Internal Reference Soluting" Journal of Analytical Chemistry, vol. 34, No. 8, Part 1, Aug. 1979, pp. 1139-1162.

FIG. 2(a)

| [glucose] (mg/dl) | 10.01 | 30.02 | 50.00 | 99.99 | 147.60 |
|---|---|---|---|---|---|
| E (mV) | 65.35 | 90.20 | 107.43 | 129.04 | 146.23 |

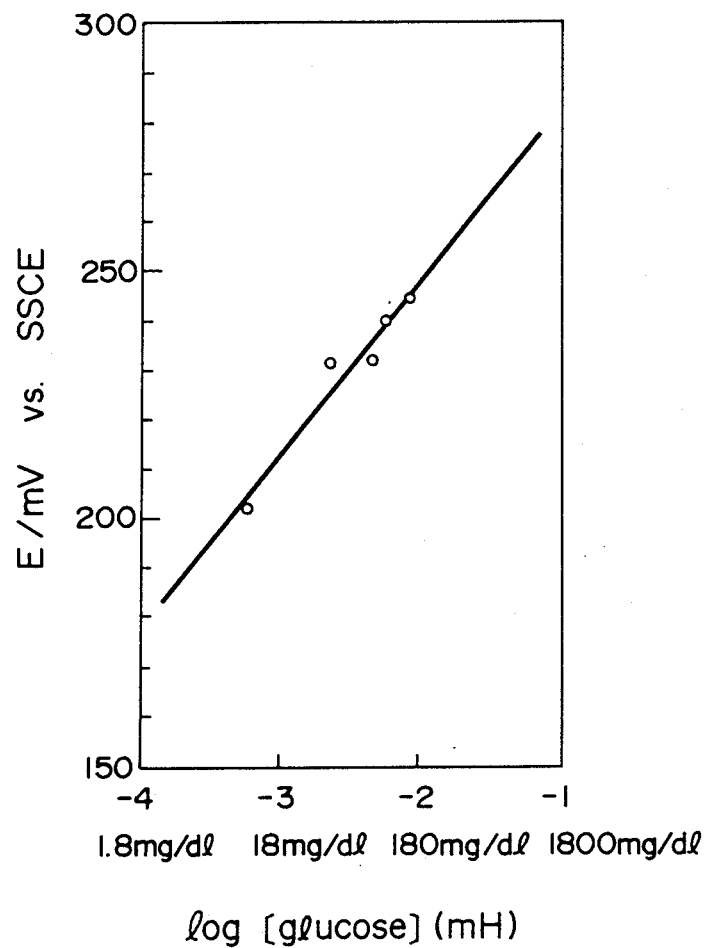
F I G. 5

ENZYME SENSOR

TECHNICAL FIELD

This invention relates to an enzyme sensor and, more particularly, to an enzyme sensor for measuring the concentration of a biological substrate by potentiometric response.

BACKGROUND ART

Examples of enzyme sensors known in the art are glucose sensors, urea sensors and uric acid sensors. These sensors are for measuring the concentration of a biological substrate after the concentration of hydrogen peroxide ($H_2O_2$) produced by an enzyme reactor or the concentration of oxygen ($O_2$) consumed by the reaction is measured amperometrically using an oxygen sensor or hydrogen peroxide sensor. For this reason, enzyme sensors generally are difficult to miniaturize. Another drawback is that these sensors cannot be utilized in enzyme reactions that are not accompanied by the consumption of oxygen or the production of hydrogen peroxide. One expedient for solving these problems is a sensor which determines the concentration of a biological substrate by measuring a change in pH that accompanies the progress of an enzyme reaction.

In recent years attempts have been made to fabricate miniature enzyme sensors by utilizing ISFET (ion-selective field-effect transistor)-type pH sensors. However, the adhesion between an enzyme film and the surface of a gate insulating film (such as a film of $Si_3N_4$, $Al_2O_3$ or $Ta_2O_5$) used in these ISFET's is poor. As a result, these sensors exhibit a somewhat low sensitivity, a large amount of drift and possess but a short service life.

DISCLOSURE OF THE INVENTION

An object of the present invention is to provide a miniature enzyme sensor for measuring the concentration of a biological substrate potentiometrically, which sensor exhibits a high sensitivity, little drift and possesses a long service life.

As means for solving the foregoing problems, the enzyme sensor of the present invention comprises an insulating substrate, an electrically conductive layer coating the insulating substrate, a redox layer having an oxidation-reduction function coating a surface of the electrically conductive layer, and an enzyme-fixed layer coating a surface of the redox layer and having an enzyme fixed thereto.

In another aspect, the enzyme sensor of the present invention comprises a MOSFET, an electrically conductive layer coating a gate insulating film of the MOSFET, a redox layer having an oxidation-reduction function coating a surface of the electrically conductive layer, and an enzyme-fixed layer coating a surface of the redox layer and having an enzyme fixed thereto.

In the arrangement of the first aspect of the invention, the concentration of a biological substrate is converted into a corresponding hydrogen ion concentration by the enzyme-fixed layer, and the hydrogen ion concentration is converted into a corresponding electric field by the redox layer. The electric field thus produced is measured by the electrically conductive layer as a potential difference across the sensor and a reference electrode.

In the arrangement of the second aspect of the invention, the electric field is transmitted onto the gate insulating film of the MOSFET by the electrically conductive layer and is measured by the MOSFET.

The invention thus provides a miniature enzyme sensor for measuring the concentration of a biological substrate potentiometrically. The sensor exhibits a high sensitivity, little drift and possesses a long service life.

More specifically, the enzyme sensor of the present invention has the following advantages:

(1) Since the enzyme sensor is constructed on the gate portion of an ISFET, the sensor can be ultra-miniaturized and adapted for multiple enzymes.

(2) Since the the redox layer is used as a pH-sensitive film, sensitivity is high. (3) Since film formation is carried out by electrolytic polymerization, adhesion is excellent and film formation with good adhesion is possible even on irregular portion of the electrically conductive substrate. As a result, the sensor excels in durability and has a long lifetime.

(4) Since the enzyme is fixed using electrolytic polymerization, enzyme fixation is excellent and the enzyme-fixed film obtained exhibits excellent adhesion and durability.

(5) Since measurement is performed potentiometrically, the enzyme sensor is capable of utilizing an enzyme reaction in which oxygen does not participate.

(6) Since measurement is performed potentiometrically, there is little electrical leakage in living bodies and in the measurement system. The sensor therefore is safe to use.

(7) Since film formation is by electrolytic polymerization, film thickness can be readily controlled.

BRIEF DESCRIPTION OF THE DRAWINGS

FIG. 5 is a view illustrating the results of measurements in accordance with first comparative example of an enzyme sensor.

BEST MODE FOR CARRYING OUT THE INVENTION

Embodiments of the present invention will now be described in detail with reference to the drawings.

In accordance with the invention, an enzyme electrode was fabricated by directly applying a coating of a redox layer (as by electrolytic polymerization) to a substrate obtained by depositing an electrically conductive layer (such as iridium oxide, ITO, platinum, palladium oxide or silver, which exhibit an oxidation-reduction reaction) on an insulating substrate (such as sapphire, diamond, $SiO_2$, $Si_3N_4$, $Ta_2O_5$), and coating the result with enzyme-fixed layer (fabricated in accordance with a conventional enzyme fixing process or by carrying out an enzyme fixing reaction using an electrolytic reaction process in a reaction film for fixing an enzyme-fixed film, an example of the reaction film being one in which 1,2 diaminobenzene and pyrrole coexist), the potential difference across the enzyme electrode serving as an active electrode and a reference electrode (a saturated sodium calomel electrode) was measured, and the electrical characteristics due to the layers arranged as set forth above as well as the physical characteristics of these layers were tested. As a result, the problems (i.e. the tendency for the enzyme-fixed layer to peel off the gate insulating film, the reduced sensitivity, the large drift and the short service life) encountered when using a conventional enzyme sensor obtained by coating an ISFET with an enzyme-fixed layer were able to be solved. The slope of the Nernst equation, which is a typical characteristic, was more than 58 mV/pH (theoretically 60.54 mV/pH at 32° C.), thus closely approximating the theoretical equation. A high sensitivity of 73.87 mV/pH was obtained in the case of enzyme fixation when joint use was made of 1,2 diaminobenzene. In comparison, the slope of the Nernst equation for an enzyme sensor fabricated by directly coating an electrically conductive layer (e.g. iridium oxide) with an enzyme without an oxidative polymerization layer (a redox layer) was only 35.40 mV/pH, indicating a very low sensitivity.

EXAMPLE 1

Figure 1A:
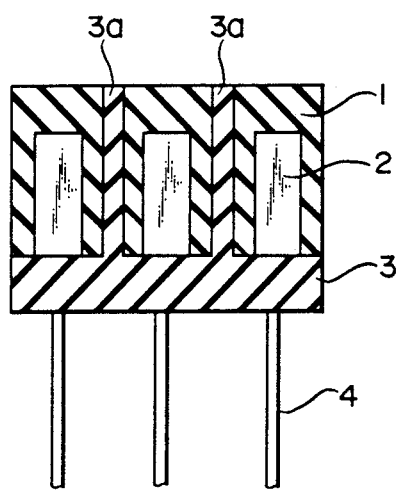
FIG. 1(a) is a schematic view showing the construction of an iridium oxide electrode.
Figure 1B:
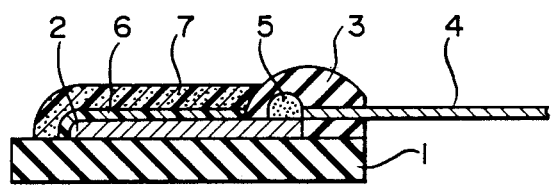
FIG. 1(b) is a schematic sectional view of an enzyme sensor.

FIGS. 1(a), (b) are schematic views illustrating the construction of an enzyme sensor fabricated in accordance with the present embodiment.

(1) Iridium oxide electrode

An iridium oxide layer 2 having an area of 3 mm×12 mm and a thickness of 1000 Å was deposited, by means of sputtering, at three locations spaced apart by 3.2 mm on the surface of a sapphire substrate 1 having an area of 20 mm×18 mm and a thickness of 1.5 mm. Leads 4 were connected to respective ones of the iridium oxide layers 2 by an electrically conductive adhesive 5 (Cyclone B, manufactured by Atsugi Central Laboratories K.K.) at locations 3 mm from the terminuses of the iridium oxide layers. Each connection was coated with an epoxy adhesive 3 (Araldyde, manufactured by Chiba Gaigi K.K.). The connections where thus insulated from the outside. A wall 3a was formed between mutually adjacent ones of the iridium oxide layers 2 by the same adhesive in order to prevent interaction between the layers 2. The resulting element was employed as an iridium oxide electrode.

(2) Redox layer

A redox layer 6 was deposited on the surface of the iridium oxide electrode by an electrolytic polymerization process. Electrolysis was carried out using a threeelectrode cell in which the iridium oxide electrode, a silver/silver chloride electrode and a platinum coil were employed as an active electrode, reference electrode and opposing electrode, respectively.

Composition of electrolyte solution

| 2,6-dimethylphenol | 20 mmol/l |
| sodium perchlorate | 0.1 mol/l |
| acetonitrile | (solvent) |

Electrolytic conditions

The electrolyzing potential was swept three times (sweep rate: 50 mV/sec) from 0 to +1.5 V (vs. Ag-/AgCl) in a nitrogen atmosphere at a temperature of −20° C., followed by carrying out constant-potential electrolysis for 10 min at a constant potential of +1.5 V. A poly(2,6-dimethylphenol) film (having a layer thickness of about 30 μm) was formed.

(3) Enzyme-fixed layer

A glucose oxidase film was deposited, through a procedure set forth hereinbelow, as an enzyme-fixed layer 7 on the surface of the redox layer 6. The film was deposited by a crosslinking process using glutaric aldehyde as a crosslinking agent.

(Solution A): 15 wt-% cow blood serum albumin was dissolved in a pH 8.04 phosphate buffer solution, and 0.5 g of glucose oxidase was dissolved in 5 ml of the resulting solution.

(Solution B): 25% glutaric aldehyde aqueous solution (Solution C): 10% glycine aqeuous solution About 6 μl of the A solution per iridium oxide electrode was placed on the redox layer 6 by using a microsyringe, after which drying was allowed to take place for about 1 min. The same amount of the B solution was applied in drops, followed by 1 min of drying. The electrode was then dipped into Solution C for about 1 min, thereby removing unreacted glucose oxidase A glucose oxidase layer was thus deposited as the enzyme-fixed layer 7.

EXAMPLE 2

(1) Iridium oxide electrode

An iridium oxide electrode similar to that of Example 1 was formed.

(2) Redox layer

The redox layer 6 was deposited on the surface of the iridium oxide electrode through a process similar to that used in Example 1.

(3) Enzyme layer

By a process described herein below, glucose oxidase was incorporated in a 1,2-diaminobenzene electrolytic polymerization film and the enzyme-fixed layer 7 was deposited on the redox layer 6.

Using the iridium oxide electrode coated with the redox layer 6 as an active electrode, a silver/silver chloride electrode as a reference electrode and a platinum coil as an opposing electrode, electrolytic polymerization was carried out in an aqueous solution of 1,2-diaminobenzene containing glucose oxidase. As a result, an electrolytic polymerization film of the 1,2-diaminobenzene was formed and, at the same time, the coexisting glucose oxidase was incorporated in the film and the glucose oxidase film was deposited.

Composition of electrolyte solution

| glucose oxidase | 1 mg/1 ml |
| 1,2-diaminobenzene | 20 mM |
| sodium perchlorate | 0.5 M |
| water | solvent |

Electrolytic conditions

The electrolyzing potential was swept three times (sweep rate: 50 mV/sec) from 0 to +1.5 V (vs. Ag-/AgCl) in a nitrogen atmosphere, followed by carrying out constant-potential electrolysis for 30 min at a constant potential of +1.5 V.

EXAMPLE 3

(1) Iridium oxide electrode
An iridium oxide electrode similar to that of Example 1 was formed.

(2) Redox layer
The redox layer 6 was deposited on the surface of the iridium oxide electrode through a process similar to that used in Example 1.

(3) Enzyme layer
With use of pyrrole instead of 1,2-diaminobenzene, a glucose oxidase film was deposited as the enzyme-fixed layer 7 on the redox layer 6 through a process similar to that used in Example 2.

Experiment 1

The glucose concentration of a liquid specimen was changed and the response to this change exhibited by the enzyme sensor prepared in accordance with Example 1 was investigated. This was done by measuring the potential difference across a reference electrode (a saturated sodium chloride calomel electrode) and the enzyme sensor prepared in Example 1. The temperature of the liquid specimen was set at 32° C., and the pH was adjusted to 6.86 by a phosphate buffer solution. The change in potential was measured while varying concentration by adding 500 mg/dl of an aqueous glucose solution dropwise to 10 mg/dl of an aqueous glucose solution. Measurement was performed 10 min after the dropwise addition of the glucose solution when the potential had stabilized.

Figure 2B:
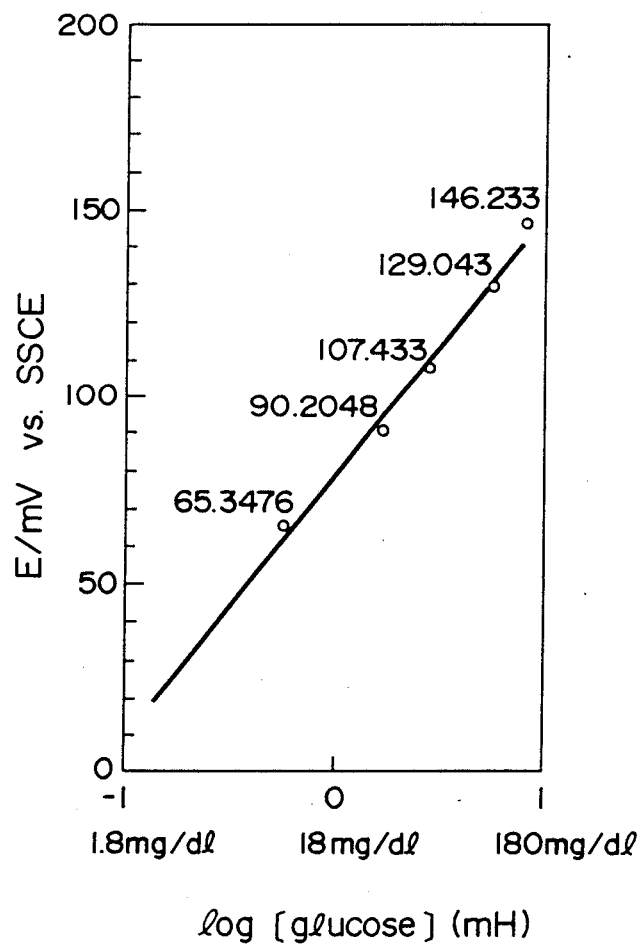
FIGS. 2(a), (b) are views illustrating the results of measurements in accordance with a first example of an enzyme sensor.

The results obtained are shown in FIG. 2(a). A plot of electrode potential vs. the logarithm of the prevailing glucose concentration is shown in FIG. 2(b). The graph shows excellent linearity between the logarithm of glucose concentration and the potential of the enzyme sensor.

The approximate expression is as follows:

$$E(mV) = 79.22 + 68.70 \log (\text{glucose})$$

Experiment 2

Figure 3:
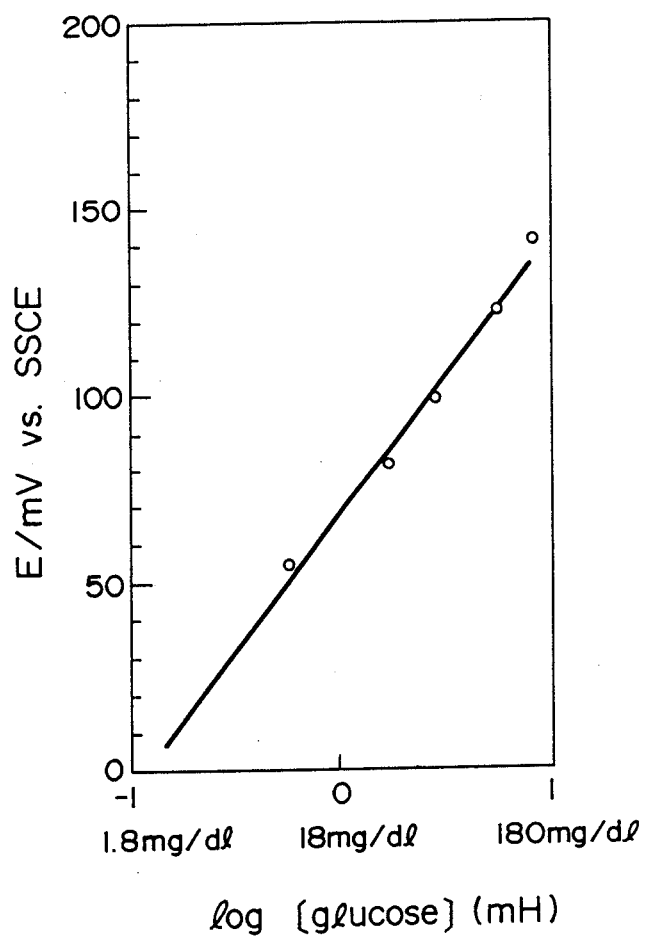
FIG. 3 is a view illustrating the results of measurements in accordance with a second example of an enzyme sensor.

Measurement similar to that in Experiment 1 was performed using the enzyme sensor prepared in accordance with Example 2. The results are shown in FIG. 3. The linear approximate expression is as follows:

$$E(mV) = 69.22 + 73.87 \log (\text{glucose})$$

Experiment 3

Figure 4:
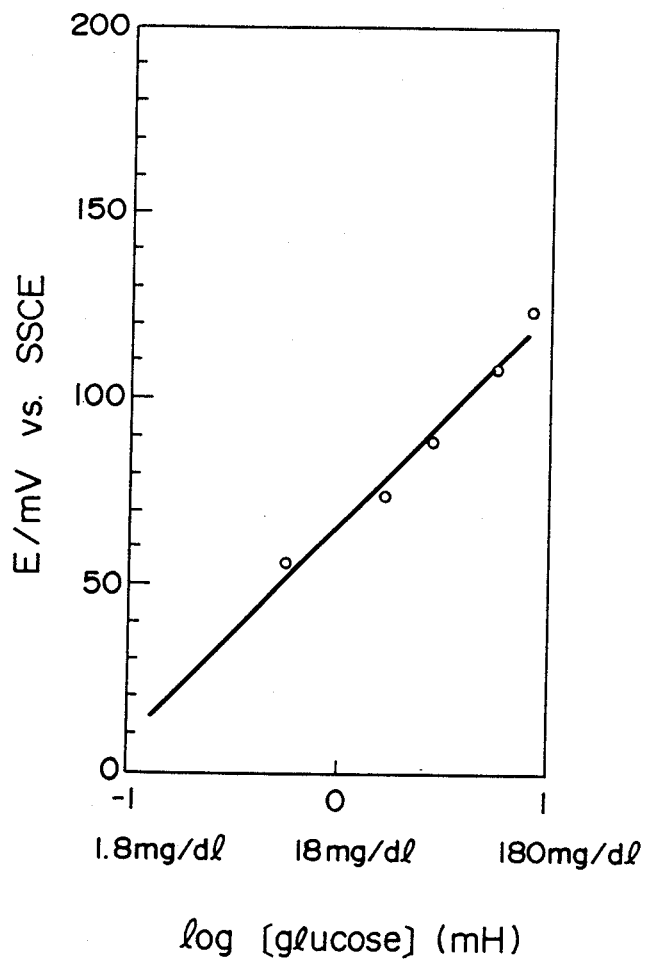
FIG. 4 is a view illustrating the results of measurements in accordance with a third example of an enzyme sensor.

Measurement similar to that in Experiment 1 was performed using the enzyme sensor prepared in accordance with Example 3. The results are shown in FIG. 4. The linear approximate expression is as follows:

$$E(mV) = 65.46 + 57.59 \log (\text{glucose})$$

Comparison Example 1

For comparison purposes an iridium oxide electrode was directly coated with an enzyme-fixed layer to fabricate an enzyme sensor which, in other aspects, was identical with the enzyme sensor of Example 1. This sensor was subjected to the measurement just as in Experiment 1. Though a substantially linear relationship is obtained between the log of glucose concentration and the potential response of the enzyme sensor, as shown in FIG. 5, the approximate expression is $$E(mV) = 319.31 + 35.40 \log (\text{glucose})$$

It will be appreciated that the slope is small in comparison with the enzyme sensors of Examples 1, 2 and 3.

EXAMPLE 4

Figure 6A:
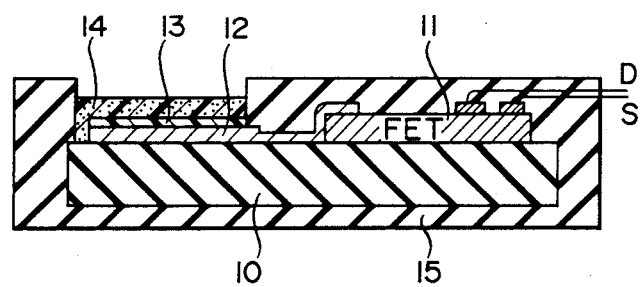
FIGS. 6(a), (b) are schematic sectional views illustrating enzyme sensors utilizing a FET in a fourth example.

An enzyme sensor was fabricated as shown in FIG. 6(a). Specifically, a MOSFET 11 was formed on a sapphire substrate 10 by utilizing a semiconductor processing technique, an isolated gate portion 12 was then formed by depositing iridium oxide on the substrate at a portion thereof spaced slightly away from the MOSFET 11 using a reactive sputtering process, a redox layer 13 and an enzyme-fixed layer 14 were formed just as in Examples 1 through 3, and the resulting element, with the exception of the isolated gate 12, was coated with an insulator 15. The enzyme sensor thus fabricated exhibited a high sensitivity of 60—70 mV/decade, similar to the sensitivities obtained in Experiments 1 through 3.

Figure 6B:
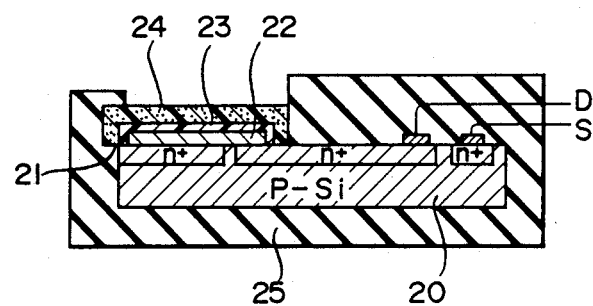

It is also possible to produce an enzyme sensor of the kind shown in FIG. 6(b). Here the enzyme sensor is obtained by forming an electrically conductive layer 22 (such as iridium oxide) on the surface of a gate insulating film 21 (a film of $SiO_2/Si_3N_4$) of a MOSFET 20, forming a redox layer 23 on the conductive layer 22, forming an enzyme-fixed layer 24 on the redox layer 23, and coating the element with an insulator 25, leaving the layer 24 exposed.

Though the invention has been described in connection with an embodiment in which iridium oxide is employed as the electrically conductive layer, similar results can be obtained using ITO, platinum, palladium oxide and silver as the electrically conductive layer Further, the invention has been described in connection with an embodiment in which a FET sensor is obtained by coating an enzyme electrode and the gate insulation film of a MOSFET formed on a sapphire substrate with layers. However, an enzyme sensor having high sensitivity, little drift and a prolonged service life can be fabricated by applying coatings consisting of an electrically conductive layer, a redox layer and an enzyme fixed layer, as illustrated in the embodiment, and the method of measuring the electric field produced in accordance with the concentration of the biological substrate is not limited to the method of the embodiment.

What is claimed is:

1. An enzyme sensor characterized by comprising:
   an insulating substrate;
   an electrically conductive layer coating said insulating substrate;
   a redox layer having an oxidation-reduction function formed on a surface of said electrically conductive layer by an electrolytic oxidative polymerization process; and
   an enzyme-fixed layer coating a surface of said redox layer and having an enzyme fixed thereto.

2. The enzyme sensor according to claim 1, characterized in that said insulating substrate is selected from among substances exhibiting an insulating property.

3. The enzyme sensor according to claim 1, characterized in that said electrically conductive layer is selected from among substances manifesting an oxidation-reduction reaction.

4. The enzyme sensor according to claim 1, characterized in that said redox layer is a layer sensitive to hydrogen ion concentration.

5. The enzyme sensor according to claim 1, characterized in that said enzyme layer is formed by an electrolytic (oxidative) polymerization process.

6. The enzyme sensor according to claim 1, characterized in that said enzyme-fixed layer is formed by a crosslinking process or by an incorporating process.

7. An enzyme sensor characterized by comprising:
a MOSFET:
an electrically conductive layer coating a gate insulating film of said MOSFET;
a redox layer having an oxidation-reduction function formed on a surface of said electrically conductive layer by an electrolytic oxidative polymerization process; and
an enzyme-fixed layer coating a surface of said redox layer and having an enzyme fixed thereto.

8. The enzyme sensor according to claim 7, characterized in that said electrically conductive layer is selected from among substances manifesting an oxidation-reduction reaction.

9. The enzyme sensor according to claim 7, characterized in that said electrically conductive layer is an isolated gate formed at a small distance from a FET portion.

10. The enzyme sensor according to claim 7, characterized in that said redox layer is a layer sensitive to hydrogen ion concentration.

11. The enzyme sensor according to claim 7, characterized in that said enzyme-fixed layer is formed by an electrolytic (oxidative) polymerization process.

12. The enzyme sensor according to claim 7, characterized in that said enzyme-fixed layer is formed by a crosslinking process or by an incorporating process.

* * * * *